(12) United States Patent
Schwarz et al.

(10) Patent No.: US 10,369,331 B2
(45) Date of Patent: Aug. 6, 2019

(54) POSITIONING DEVICE FOR A MEDICAL CATHETER

(71) Applicant: Urotech GmbH, Rohrdorf-Achenmuehle (DE)

(72) Inventors: Werner Schwarz, Ruhpolding (DE); David Hauser, Rosenheim (DE); Christopher Janssen, Thedinghausen-Wulmstorf (DE)

(73) Assignee: Urotech GmbH, Rohrdorf-Achenmuehle (DE)

( * ) Notice: Subject to any disclaimer, the term of this patent is extended or adjusted under 35 U.S.C. 154(b) by 636 days.

(21) Appl. No.: 15/023,793

(22) PCT Filed: Sep. 23, 2014

(86) PCT No.: PCT/DE2014/000481
§ 371 (c)(1),
(2) Date: Mar. 22, 2016

(87) PCT Pub. No.: WO2015/043569
PCT Pub. Date: Apr. 2, 2015

(65) Prior Publication Data
US 2016/0213883 A1 Jul. 28, 2016

(30) Foreign Application Priority Data
Sep. 24, 2013 (DE) .......................... 10 2013 015 845

(51) Int. Cl.
*A61M 25/01* (2006.01)
*A61M 25/02* (2006.01)
(Continued)

(52) U.S. Cl.
CPC ..... *A61M 25/0113* (2013.01); *A61M 25/0105* (2013.01); *A61M 25/0136* (2013.01);
(Continued)

(58) Field of Classification Search
CPC ...... A61M 25/0113; A61M 2025/0293; A61M 25/0105; A61M 25/0147; A61M 25/0136; A61M 37/0069
See application file for complete search history.

(56) References Cited

U.S. PATENT DOCUMENTS 4,713,057 A * 12/1987 Huttner ............. A61M 25/0612
604/164.07
6,053,899 A    4/2000 Slanda et al.
(Continued)

FOREIGN PATENT DOCUMENTS

DE    201 13 815 U1    11/2001
DE    698 31 342 T2    6/2006
(Continued)

OTHER PUBLICATIONS

English translation of EP 1459780.*
International Search Report of PCT/DE2014/000481, dated Feb. 23, 2015.

*Primary Examiner* — Jason E Flick
*Assistant Examiner* — Courtney B Fredrickson
(74) *Attorney, Agent, or Firm* — Collard & Roe, P.C.

(57) ABSTRACT

A positioning device for a medical catheter to be positioned in a bodily orifice or cavity, the device containing an elongated tubular or sleeve-type catheter receiving member, one end of which receives the catheter to be positioned, elongated catheter release member which is held inside or outside the catheter receiving member and which can be displaced in the longitudinal direction of the member and a motion mechanism comprising a motion conversion device, by means of which the catheter receiving member and the catheter release member can be displaced relative to one another in the longitudinal direction of the device, thus releasing the catheter from the catheter receiving member; the motion conversion device has an actuating member, by
(Continued)

means of which motion that is carried out transversely to the longitudinal direction of the device or pivoting motion can be converted into longitudinal motion running in the longitudinal direction of the device.

5 Claims, 6 Drawing Sheets

(51) Int. Cl.
*A61M 37/00* (2006.01)
*A61M 27/00* (2006.01)

(52) U.S. Cl.
CPC ....... *A61M 25/0147* (2013.01); *A61M 27/008* (2013.01); *A61M 37/0069* (2013.01); *A61M 2025/0293* (2013.01)

(56) References Cited

U.S. PATENT DOCUMENTS

| | | | | |
|---|---|---|---|---|
| 6,796,976 | B1 * | 9/2004 | Chin | ................... A61M 25/01 |
| | | | | 604/164.07 |
| 8,292,939 | B2 | 10/2012 | Yachia et al. | |
| 8,870,855 | B2 | 10/2014 | Fargahi | |
| 2005/0101967 | A1 * | 5/2005 | Weber | ................... A61F 2/167 |
| | | | | 606/107 |
| 2011/0245864 | A1 | 10/2011 | Besse et al. | |

FOREIGN PATENT DOCUMENTS

| | | | |
|---|---|---|---|
| EP | 1 459 780 A1 | 9/2004 | |
| EP | 1459780 A1 * | 9/2004 | ........ A61M 25/0113 |
| EP | 2 371 308 A2 | 10/2011 | |
| EP | 2 604 231 A2 | 6/2013 | |
| WO | 2007/029242 A1 | 3/2007 | |

\* cited by examiner

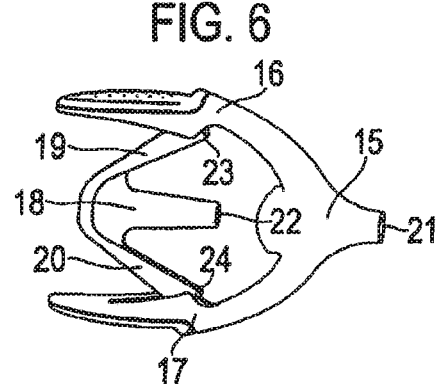
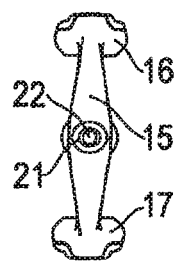
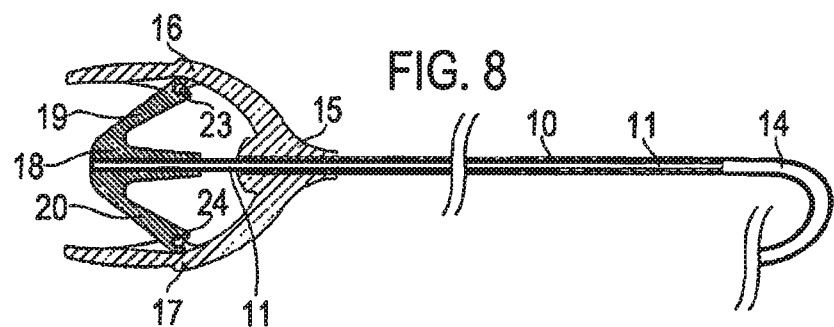
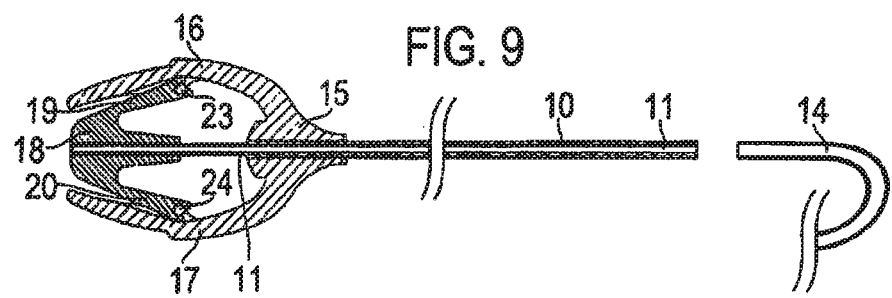

POSITIONING DEVICE FOR A MEDICAL CATHETER

CROSS REFERENCE TO RELATED APPLICATIONS

This application is the National Stage of PCT/DE2014/000481 filed on Sep. 23, 2014, which claims priority under 35 U.S.C. § 119 of German Application No. 10 2013 015 845.1 filed on Sep. 23, 2013, the disclosures of which are incorporated by reference. The international application under PCT article 21(2) was not published in English.

The present invention relates to a positioning apparatus for a medical catheter to be positioned in a body opening or body cavity of an individual, comprising an elongated tubular or hose-shaped catheter accommodation member, by one end of which the catheter to be positioned can be accommodated, an elongated catheter release member accommodated within or outside of the catheter accommodation member and displaceable in the longitudinal direction of the latter, and a movement mechanism provided between the catheter accommodation member and the catheter release member, having a movement conversion device by means of which the catheter accommodation member, with the catheter accommodated by the latter, and the catheter release element can be displaced relative to one another in a longitudinal apparatus direction, with release of the catheter from the catheter accommodation member.

A positioning apparatus of the type stated above is already known (EP 1 459 780 B1). This known positioning apparatus consists of a holding apparatus, configured to be elongated, which can be releasably connected with the catheter at its one end, which holding apparatus is enclosed by a pusher hose in such a manner that during use, a distal end of the pusher hose comes to lie in the region of the end of the catheter. In this regard, the pusher hose can be displaced coaxially relative to the holding apparatus, by means of a movable pusher element, in such a manner that during a displacement of the pusher hose in the distal direction, the end of the catheter can be released from the distal end of the holding apparatus, and the pusher element, the holding apparatus, and the pusher hose are disposed, at least in part, within the housing, which has at least one distal opening for exit of the holding apparatus and/or of the pusher hose.

In this regard, the housing consists of an upper housing part and a lower housing part. The upper housing part and the lower housing part are configured so that they can rotate relative to one another, and at least one guide for guidance of at least one engagement element configured on the pusher element is disposed on an inside circumference of the upper housing part. The guide has at least two engagement recesses for accommodation of the engagement element, and the engagement recesses are configured to be offset relative to one another in the distal direction. The known positioning apparatus in question makes it possible, by means of performing a rotational movement between the upper housing part and the lower housing part, to impart a longitudinal movement to the pusher hose, by means of which movement the catheter can be released from the distal end of the holding apparatus. However, performance of the said rotational movement normally requires two-handed operation of the known positioning apparatus in question.

An apparatus for implantation of a catheter formed by a ureter splint in a ureter is also already known (DE 201 13 815 U1). This known application set comprises an outer cannula, a head piece that is firmly connected with the one end of the outer cannula, a handle sleeve that is releasably connected with the head piece, and a longitudinal slot that is open toward the one end of the handle sleeve. Furthermore, an inner cannula is provided, which is disposed so as to be axially displaceable in the outer cannula and extends through the handle sleeve. Moreover, an activation element pressed in the direction of the head piece by a spring, preferably configured as a pressure spring, which element is firmly connected with the inner cannula, projects through the longitudinal slot of the handle sleeve and is guided in the latter. What is more, an end piece is releasably connected with the handle sleeve. However, application of a ureter splint in a ureter normally requires two-handed operation of the known application set in question here, as well.

Sometimes, however, the desire exists to be able to operate medical catheters to be placed in body openings or body cavities of individuals with only one hand, in each instance. The invention is therefore based on the task of configuring a positioning apparatus of the type stated initially in such a manner that it allows one-handed operation.

The task stated above is accomplished, in the case of a positioning apparatus of the type stated initially, according to the invention, in that the movement conversion device has an activation member by means of which a transversal movement or a pivoting movement exerted transverse to the said longitudinal apparatus direction can be converted into a longitudinal movement that runs in the said longitudinal apparatus direction.

From this, the advantage results that one-handed operation of the positioning apparatus is possible with relatively little effort. After the positioning apparatus according to the invention has been accommodated in the hand surface of an operating hand of an operator, the activation member can then be easily activated using the thumb of the hand in question, for example, in order to release the catheter from the catheter accommodation member after placement at a desired location.

Preferably, the movement conversion device has a drive element that is coupled with the catheter accommodation member or the catheter release member, which element contains at least one contact surface or guide track that runs at a slant to the said longitudinal apparatus direction, and has the activation member that is coupled with the catheter release member or the catheter accommodation member, which activation member can be activated transverse to the said longitudinal apparatus direction, acting on the respective contact surface or guide track, and by means of which activation member the drive element is displaceable in the longitudinal apparatus direction in question, by the member being activated and acting on the respective contact surface or guide track. The advantage of a relatively low design effort for implementation of the movement conversion device results from this.

According to a practical embodiment of the invention, the activation member has two pressing parts that are connected with one another by means of a connection part and can be compressed in the direction toward the latter, and the connection part is firmly connected with the catheter accommodation member or the catheter release member; the catheter release member or the catheter accommodation member has at least one bearing journal that projects away from it and is accommodated in a related guide track of the activation member, the guide track of which possesses a progression such that the catheter release member and the catheter accommodation member are displaceable relative to one another in the said longitudinal apparatus direction in response to compression of the two arm parts. The advantage of a positioning apparatus that can be produced in particularly simple manner, in total, for one-handed operation results from this.

Preferably, in the practical embodiment of the invention considered above, the two pressing parts have side parts that project away from them at an angle, in which parts a guide track for accommodation of a bearing journal is accommodated, in each instance, and the two guide tracks run in opposite directions with reference to the said longitudinal apparatus direction. The positioning apparatus according to the invention can be implemented in particularly simple manner as a result.

It is practical if the two pressing parts can be protected by a releasable securing part that blocks their unintentional movement. The advantage of a positioning apparatus that can be handled in particularly reliable manner results from this.

According to a particularly practical further development of the invention, the securing part, as an insertion part, can be releasably accommodated by an opening formed between the two pressing parts. This advantageously allows particularly simple unlocking of the positioning apparatus. Specifically, for this purpose the securing part merely has to be taken out of the opening in question, which is preferably a passage opening.

According to a further practical embodiment of the invention, the activation member has two pressing parts that are connected with one another by means of a connection part and can be compressed in the direction toward this part, and the connection part is firmly connected with the catheter accommodation member or the catheter release member; the catheter release member or the catheter accommodation member is coupled with the pressing parts by means of articulation members. The advantage of a positioning apparatus that can be produced in particularly simple manner results from this, as well. In this regard, the articulation members can be formed on the two pressing parts and the connection part in such a manner that all of these elements are formed by a single cohesive part.

In a special configuration of the pressing parts and of the connection part, the articulation members preferably have a support part firmly connected with the catheter release member or the catheter accommodation member, and support arms that project away from the support part, which arms are connected, in articulated manner, with coupling elements of the activation member. In this way, an articulation arrangement can be implemented between the two pressing parts and the connection part, in particularly simple manner, which arrangement is suitable for a plurality of repeated articulation movements, without problems. A placement apparatus structured in this manner can then easily be used for repeated applications.

According to another practical embodiment of the invention, the catheter accommodation member or the catheter release member is firmly connected with a holder, and the catheter release member or the catheter accommodation member is provided, in the holder, with a journal arrangement that has at least one bearing journal; in this regard, the journal arrangement is preferably accommodated in at least one guide track of an activation member that can be displaced at an angle to the longitudinal apparatus direction, relative to the holder. A positioning apparatus having such a structure can also be implemented in particularly simple manner for one-handed operation.

Preferably, in the practical embodiment of the invention last considered, the activation member is accommodated in the holder and can be displaced in it at a right angle to the said longitudinal apparatus direction. Such an angle position of the activation member advantageously allows particularly easy one-handed operation of the positioning apparatus according to the invention that is in question.

According to yet a further practical embodiment of the invention, the movement conversion device for conversion of a pivoting movement into the longitudinal movement that runs in the said longitudinal apparatus direction, as an activation member, has a pivoting member coupled with the catheter release member or the catheter accommodation member, which pivoting member can be pivoted relative to an accommodation body connected with the catheter accommodation member or the catheter release member. The advantage of a positioning apparatus for one-handed operation, which can be implemented in relatively simple manner, results from this, as well.

Preferably, in the practical embodiment of the invention last considered, the pivoting member can be pivoted in the said longitudinal apparatus direction relative to the accommodation body. A positioning apparatus structured in this manner can also be operated particularly easily with one hand, for positioning of a catheter at a desired location.

According to yet another practical embodiment of the invention, a radiation-sensitive detection layer is provided between the catheter accommodation member and the catheter release member. This brings with it the advantage that the distal end region of the positioning apparatus according to the invention, by which the catheter to be positioned in an individual is supported, can be made visible on a monitor by means of an imaging method. Preferably, the radiation sensitivity for X-rays is utilized here. For this purpose, the radiation-sensitive detection layer in question consists of gold, platinum or of a platinum-iridium alloy, which is applied either on the outside of the catheter accommodation member or on the inside of the catheter release member.

Using drawings, the invention will be explained below, on the basis of four concrete exemplary embodiments of a positioning apparatus according to the invention.

FIG. 6 shows, in a side view, not to scale, a second exemplary embodiment of a positioning apparatus according to the invention, in the non-compressed state.

FIG. 7 shows the positioning apparatus shown in FIG. 6 in a front view.

FIG. 8 shows, in a sectional view, not to scale, the positioning apparatus shown in FIG. 6, in the non-compressed state.

FIG. 9 shows, in a sectional view, not to scale, the positioning apparatus shown in FIG. 6, in a compressed state.

Before the drawings are discussed in greater detail, it should first of all be noted that corresponding parts or elements are labeled with the same reference symbols in all the drawing figures.

Figure 1:
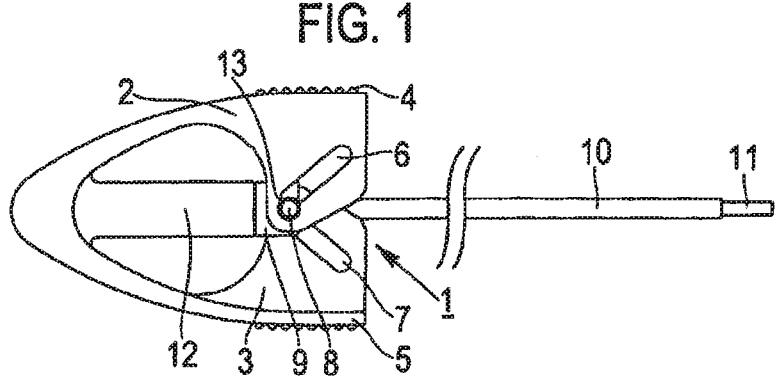
FIG. 1 shows, in a side view, not to scale, a first exemplary embodiment of a positioning apparatus according to the invention.

FIG. 1 shows, in a side view, a first embodiment of a positioning apparatus 1 according to the invention. The positioning apparatus 1 consists of a two-part activation body that has—as is evident in greater detail from FIGS. 2 and 3—two side parts 2 and 3 that run parallel at a slight distance from one another, which parts are connected with one another at their one ends—these are their ends shown on the left in FIG. 1. Here, pressing parts 4 and 5, respectively, Project away from the two side parts 2, 3, running at a right angle from them, which pressing parts run in the direction of the other side part 3 or 2, respectively, in each instance.

Figure 4:
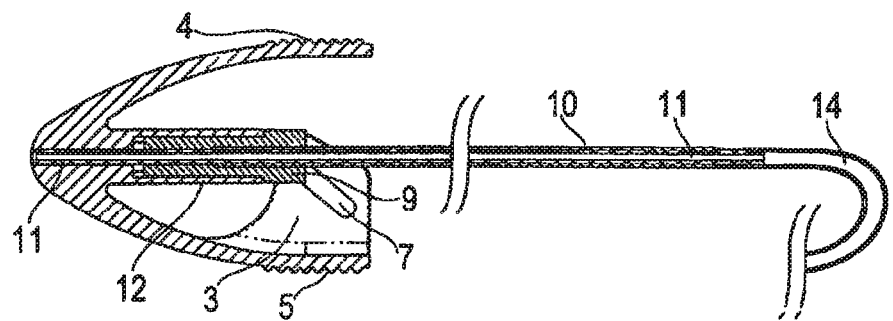
FIG. 4 shows, in a sectional view, not to scale, the positioning apparatus shown in FIG. 1, in the non-compressed state.
Figure 5:
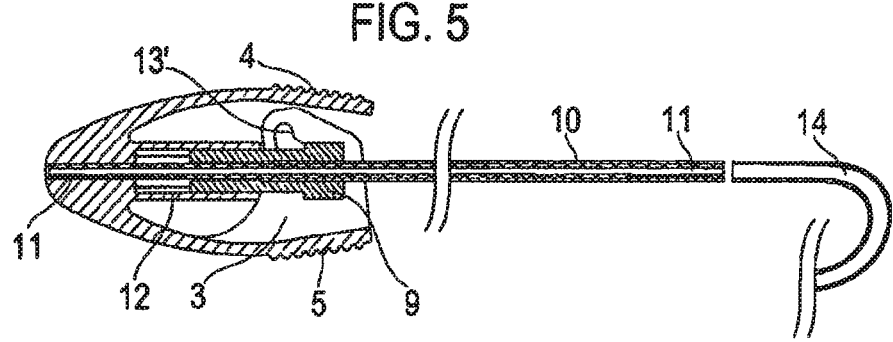
FIG. 5 shows, in a sectional view, not to scale, the positioning apparatus shown in FIG. 1, in a compressed state.

A support part 12 that projects into the interstice between the two pressing parts 4, 5 extends in from the connection region, not indicated in greater detail in FIG. 1, of the one aforementioned ends of the side parts 2, 3, by which support part a drive element 9 is displaceably accommodated, as is evident in greater detail from the sectional views according to FIGS. 4 and 5. This drive element 9 is formed by a cylindrical part here, from which at least one bearing journal 8 projects transverse to the longitudinal apparatus direction, which journal is guided in a guide track 6 or 7, which is situated in the side part 2 or 3 that faces the bearing journal in question. In the present case, two such bearing journals 8 project from the drive element 9 from diametrically opposite locations. These bearing journals 8 are guided in guide tracks 6, 7, which run in opposite directions with reference to the longitudinal apparatus direction of the positioning apparatus 1, as is evident from FIG. 1. A guide track depression 13 is furthermore shown in the guide track 6; its significance will be discussed in greater detail below.

The positioning apparatus 1 furthermore comprises a catheter accommodation member 11, which is accommodated by a catheter release member 10 here. These two members 11 and 10 will be discussed in greater detail below.

At this point, it should be noted that the guide tracks 6, 7 can be replaced with simple guide surfaces, if necessary, which run in the same directions as the guide tracks 6, 7. By the way, the aforementioned longitudinal apparatus direction mentioned is understood to be the longitudinal direction of the respective positioning apparatus within the scope of this application, and thereby the direction in which the catheter accommodation member 11 and the catheter release member 10 run.

The structure of the positioning apparatus 1 explained above, using FIGS. 1, 2, and 3, with the side parts 2, 3, the pressing parts 4, 5, the guide tracks 6, 7, the bearing journals 8, the drive element 9, and the support part 12 represent a movement conversion device—as is evident in greater detail from the representations according to FIGS. 4 and 5. In this movement conversion device, the pressing parts 4, 5 represent an activation device, by means of the activation of which, in a direction transverse to the longitudinal apparatus direction, the drive element 9 is displaced relative to the support part 12, in the said longitudinal apparatus direction. This means that by means of activation, namely by means of compression of the two pressing parts 4, 5, a transversal movement that corresponds to this movement can be converted into a longitudinal movement of the drive element 9 relative to the support part 12.

The hose-shaped or cylindrical catheter accommodation member 11 is firmly connected with the support part 12 mentioned above, as is evident in greater detail from FIGS. 4 and 5. This catheter accommodation member 11 serves for releasable accommodation of the catheter 14 to be positioned (not shown in FIG. 1), which is set onto the catheter accommodation member 11 in question for this purpose. The catheter accommodation member 11 is enclosed, according to FIG. 1, by the elongated catheter release member 10, which is preferably a hose-shaped catheter release member 10. This catheter release member 10 is firmly connected with the drive element 9 in the present embodiment, which element can be displaced in the longitudinal apparatus direction relative to the support part 12.

The conversion of a transversal movement into a longitudinal movement mentioned above is clearly evident from the sectional representations of the first embodiment of the positioning apparatus 1 according to the invention, explained above using FIGS. 1, 2, and 3, as shown in FIGS. 4 and 5.

In this regard, FIG. 4 shows the state of the positioning apparatus 1 in question that can be seen in FIG. 1. In this state, the two pressing parts 4 and 5 are in the non-compressed starting state. The catheter 14, which can be a ureter splint, for example, has been set onto the catheter accommodation member 10, at the distal apparatus end shown on the right in FIG. 4, for example by means of an oblong opening contained in it.

FIG. 5 shows positioning apparatus in question in a state in which the two pressing parts 4 and 5 are compressed. A comparison of this representation with the representation shown in FIG. 4 makes it evident that the drive element 9 has been pushed out of the support part 12 by means of the compression and the thereby resulting exertion of a transversal movement with reference to the longitudinal apparatus direction of the two pressing parts 4 and 5. By means of this pushing out, the catheter release member 10 has been displaced relative to the catheter accommodation member 11, to such an extent, toward the distal apparatus end, that in the present case it ends flush with the distal end of the catheter accommodation member 11 or actually projects beyond this end. Thereby the catheter 14 has been released from the catheter accommodation member 11 by means of this longitudinal movement.

The process of release of the catheter 14 from the drive element 9 as explained above is usually undertaken only after positioning of the catheter 14 by means of the positioning apparatus 1 described, in a body cavity or body opening of an individual, has taken place. In order to prevent unintentional release of the catheter 14 from the catheter accommodation member 11 during affixation of the catheter 14 to this catheter accommodation member 11, the guide tracks 6, 7 have a guide track depression 13 or 13', respectively, at the locations at which they accommodate the bearing journals 8 in the non-activated starting position of the pressing parts 4, 5, in each instance, which depression runs practically at a right angle to the longitudinal apparatus direction. If a pressure is exerted on bearing journals 8 situated in these guide track depressions 13 or 13', in FIG. 1, 4, 5 toward the left—in other words toward the proximal apparatus end, by means of the catheter accommodation member 11, then this pressure merely leads to the result that the bearing journals 8 are pressed against the guide track depressions 13, 13'; in any case, they cannot be lifted out of the guide track depressions 13, 13' in question by means of this pressure. As a result, displacement of the catheter accommodation member 11 with reference to the catheter release member 10 is prevented in this position. Guiding the bearing journals 8 out of the guide track depressions 13, 13' is only possible by means of compression of the pressing parts 4, 5.'

In FIGS. 6, 7, 8, and 9, a second embodiment of the positioning apparatus according to the invention is illustrated. In contrast to the first embodiment illustrated in FIGS. 1, 2, 3, 4, and 5, here the movement conversion device by means of which a transversal movement can be converted into a longitudinal movement consists of two pressing parts 16, 17 and a support device 18, 19, 20 that accommodates these pressing parts 16, 17. The two pressing parts 16, 17 are connected with one another by means of a connection part 15 in their regions toward the apparatus center, around which part—as will still become evident using the sectional views according to FIGS. 8 and 9 they can be elastically compressed with one another, Here, the aforementioned support device consists of two support arms 19, 20 and a connection part 18 that connects them, around which the two support arms can be elastically compressed.

The support arms 19, 20 can fundamentally be configured cohesively in one piece with the pressing parts 16 and 17, respectively, for example as a completely cohesive injection-molded part. In the present case, however, articulation members 23, 24 are provided between the ends of the support arms 19, 20 connected with one another by means of the connection part 18 and inner articulation points of the pressing parts 16, 17. These articulation members 23, 24 consist, in each instance, of an articulation ball and an articulation socket that accommodates the latter, as the sectional views according to FIGS. 8 and 9 clearly show.

The two pressing parts 16, 17 and the support arms 18, 19 that lie within these pressing parts 16, 17 form a relatively narrow positioning apparatus—as the side view according to FIG. 7 makes evident—like the positioning apparatus shown in FIG. 1 to 5. In this regard, the connection part 15 has a passage opening 21 having a relatively large opening width (diameter) for firm accommodation of the hose-shaped catheter release member 10. The connection part 18 has a passage opening 22, which, however, has a lesser opening width (diameter) as compared with the opening width of the passage opening 21. The catheter accommodation member 11 provided for accommodation of a catheter 14 is firmly accommodated in this passage opening 22; this member is displaceably accommodated in the hose-shaped catheter release member.

The positioning apparatus according to this second embodiment is activated in the manner that is evident from the sectional views according to FIGS. 8 and 9. In the sectional view according to FIG. 8, the positioning apparatus is situated in its starting state, in which the pressing parts 16, 17 are not compressed and in which a catheter 14 is releasably accommodated by the distal end of the catheter accommodation member 11 with its one end.

If the two pressing parts 16, 17 are then compressed and brought into the state that is evident from FIG. 9, a comparison of this representation with the representation shown in FIG. 8 shows that here, too, a relative longitudinal movement between the catheter accommodation member 11 and the catheter release member 10 takes place, by means of the compression of the two pressing parts 16, 17 and the resulting exertion of a transversal movement with reference to the longitudinal apparatus direction of the two pressing parts 16 and 17, such that the distal end of the catheter release member 10 ends flush with the distal end of the catheter accommodation member 11 in the present case, or actually projects beyond this end. Thereby the catheter 14 has been released from the catheter accommodation member 11 by means of this longitudinal movement.

Figure 10:
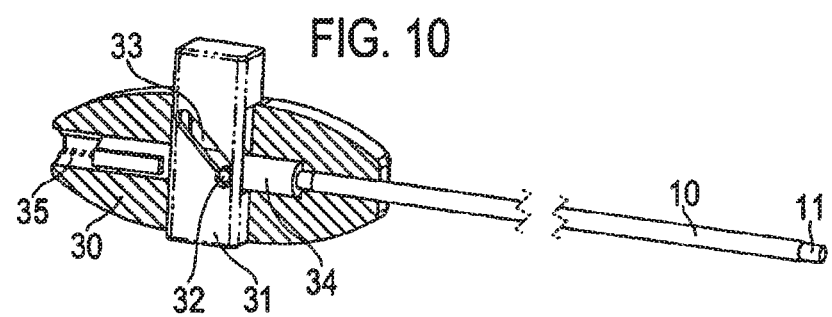
FIG. 10 shows, in a perspective view, not to scale, and partly in section, a third exemplary embodiment of a positioning apparatus according to the invention, in the non-activated state.
Figure 11:
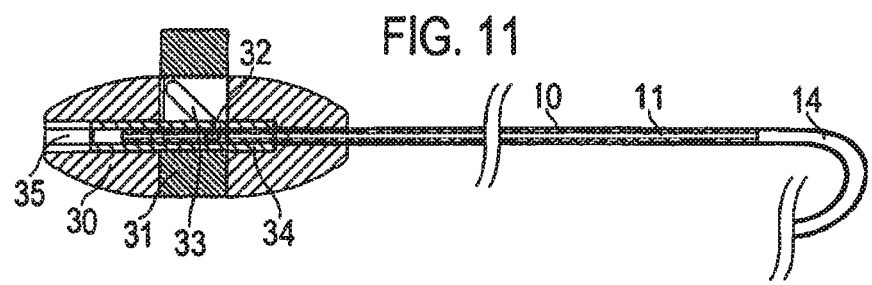
FIG. 11 shows the positioning apparatus shown in FIG. 10 in the non-activated state, in a sectional view.
Figure 12:
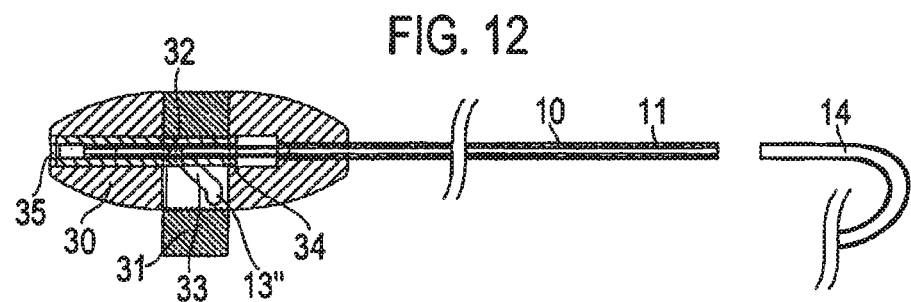
FIG. 12 shows the positioning apparatus shown in FIG. 10 in the activated state, in a sectional view.

A third embodiment of the positioning apparatus according to the invention is illustrated in FIGS. 10, 11, and 12. In contrast to the first and second embodiments considered above, here the movement conversion device, by means of which a transversal movement can be converted into a longitudinal movement, consists of a holder 30 with which the hose-shaped catheter release member 10 is firmly connected, and a key-shaped activation member 31, which can be moved at an angle, here specifically at a right angle relative to the longitudinal apparatus direction, by means of exertion of pressure.

The activation member 31 has a guide track 33 inclined at a slant relative to the longitudinal apparatus axis in at least one of its sides that lie in the plane of the drawing, by which track a bearing journal of a journal arrangement 32 is accommodated. This/These bearing journal(s) 32 is/are firmly connected with a pushing member 34, which is displaceably accommodated in an oblong hole 35 in the holder 30. The hose-shaped catheter accommodation member 11 is firmly connected with this pushing member 34; its distal end, shown on the right in FIGS. 10 and 11, serves for accommodation of a catheter 14.

When the key-shaped activation member 31 is moved, by means of pressure exertion, from the state evident from FIG. 11—in which the activation member 31 has not yet been pressed down—into the state evident from FIG. 12—in which the activation member 31 has been pressed down, the pushing member 34 has been displaced, by means of the interaction of the bearing journal(s) 32 and the guide track(s) 33, toward the proximal apparatus end, that is in FIG. 11 toward the left side. At the same time with this displacement, a retraction of the hose-shaped catheter accommodation member 11 firmly connected with the pushing member 34 has taken place, such that its distal end that lies on the right in FIG. 12 is retracted into the hose-shaped catheter release member 10 to such an extent that the catheter 14, which was previously accommodated by the distal end of the hose-shaped catheter accommodation member 11, is released from this catheter accommodation member 11.

In this third embodiment of the invention, as well, the respective guide track 33 can have a guide track depression 13" at its one end, which depression accommodates the related bearing journal 32 in the non-activated state (see FIGS. 10 and 11) of the activation member 31. The purpose of this guide track depression 13″ is the same as the one explained in connection with the guide track depressions 13, 13′ in FIG. 1 to 5.

Figure 13:
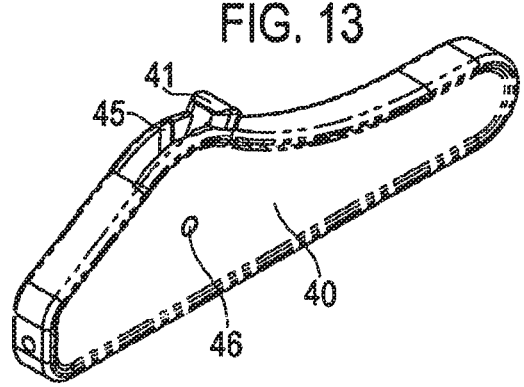
FIG. 13 shows, in a perspective view, not to scale, a fourth exemplary embodiment of a positioning apparatus according to the invention, in the non-activated state.
Figure 14:
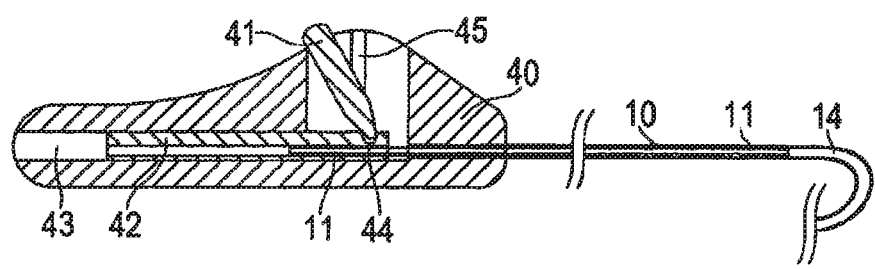
FIG. 14 shows the positioning apparatus shown in FIG. 13 in the non-activated state, in a sectional view.
Figure 15:
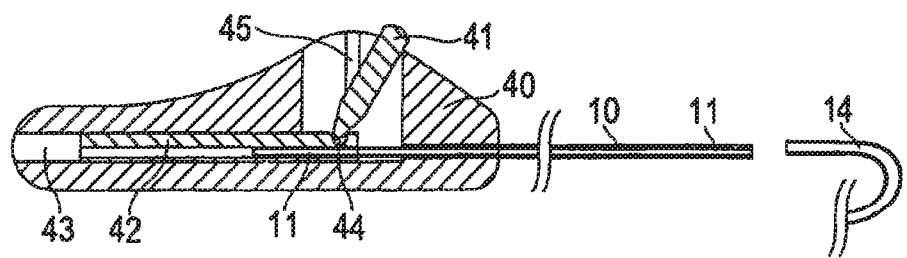
FIG. 15 shows the positioning apparatus shown in FIG. 13 in the activated state, in a sectional view.

A fourth embodiment of the positioning apparatus according to the invention is illustrated in FIGS. 13, 14, and 15. In contrast to the first, second, and third embodiments considered above, here the movement conversion device, by means of which a pivoting movement of a pivoting member or lever 41 can be converted into a longitudinal movement that takes place in the longitudinal apparatus direction, consists of a narrow accommodation body 40, with which the hose-shaped catheter release member 10 is firmly connected, and the pivoting member or lever 41 that is accommodated in an accommodation opening 45 of this accommodation body 40 so as to pivot. The lever 41, which can pivot about a bearing journal 46 shown only in FIG. 13, acts on a bearing opening 44 of a pushing member 42 in the interior of the accommodation opening of the accommodation body 40, which member is displaceably accommodated in an oblong hole 43 of the accommodation body 40 that runs in the longitudinal apparatus direction. The catheter accommodation member 11, which carries a catheter 14 at its distal end, shown on the right in FIG. 14, is firmly connected with this pushing member 42.

In FIG. 15, the pushing member 42 has been displaced toward the left, toward the proximal apparatus end, by means of moving the pivoting member or lever 41 from the starting position that can be seen in FIG. 14 into the pivoted position that can be seen in FIG. 15. At the same time with this displacement, here, too, retraction of the hose-shaped catheter accommodation member 11 that is firmly connected with the pushing member 42 has taken place, such that its distal end, which lies on the right in FIG. 15, has been retracted into the hose-shaped catheter release member 10 to such an extent that the catheter 14, which was previously accommodated by the distal end of the hose-shaped catheter accommodation member 11 has been released from this catheter accommodation member 11.

Figure 2:
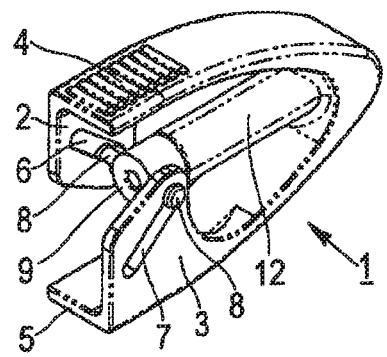
FIG. 2 shows, in a perspective view, not to scale, the positioning apparatus according to the invention shown in FIG. 1, in the non-compressed state.
Figure 3:
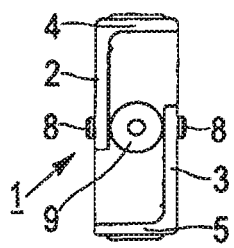
FIG. 3 shows a front view of the positioning apparatus according to the invention shown in FIG. 2.
Figure 16:
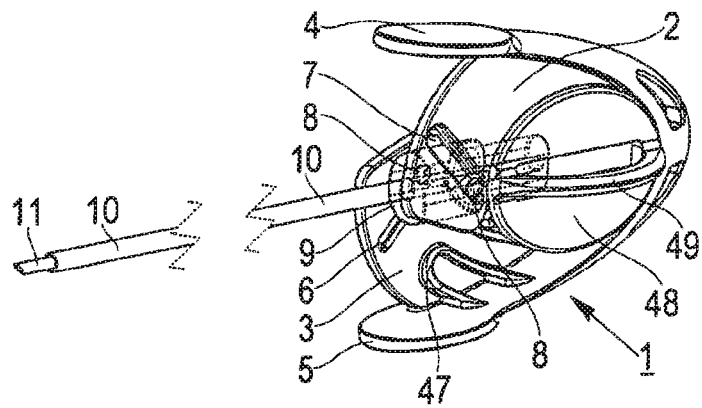
FIG. 16 shows, in a perspective view similar to FIG. 2, not to scale, a further exemplary embodiment of a positioning apparatus according to the invention, in the non-compressed state, together with a securing part.
Figure 17:
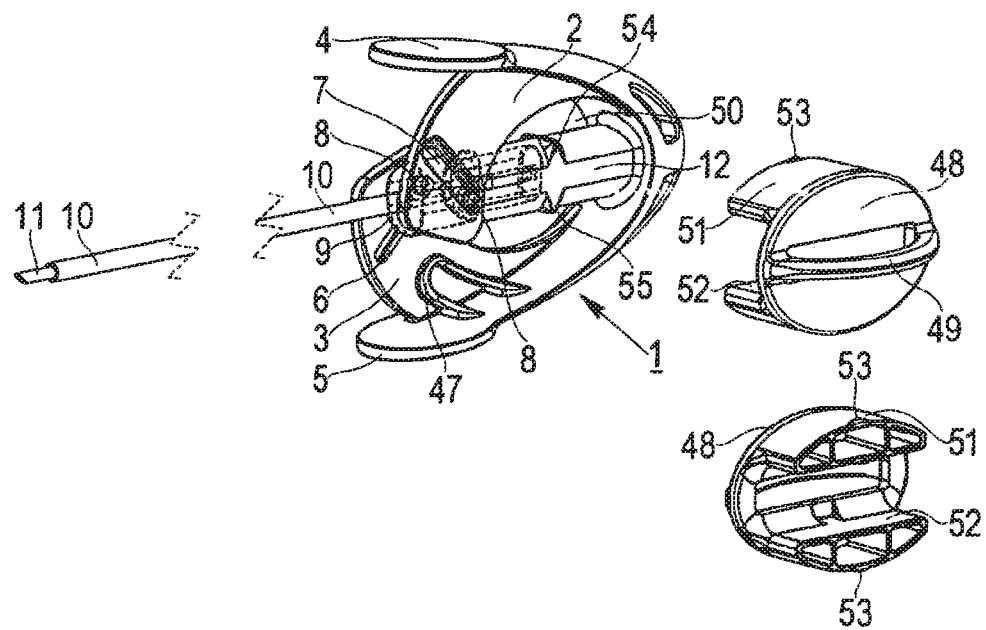
FIG. 17 shows the positioning apparatus shown in FIG. 16, with the securing part taken out, which part is shown in two different positions.

In FIGS. 16 and 17, a further exemplary embodiment of a positioning apparatus 1 according to the invention is shown in a similar perspective view, not to scale—as shown in FIG. 2—in the non-compressed state. The positioning apparatus 1, as is evident from FIGS. 16 and 17, also has two side parts 2 and 3 that run parallel at a relatively slight distance from one another, which parts are connected with one another at their one ends—these are their ends shown on the right in FIGS. 16 and 17. Here, pressing parts 4 and 5, respectively, project from the two side parts 2, 3, running at a right angle to them, which pressing parts run in the direction toward the other side part 3 or 2, respectively, in each instance.

A support part 12 that projects into an interstice between the two pressing parts 4, 5, which interstice can be seen in FIG. 17, extends in from the connection region of the one aforementioned ends of the side parts 2, 3, not indicated in any detail in FIGS. 16 and 17, by which support part a drive element 9 is displaceably accommodated, as has already been mentioned in connection with FIGS. 4 and 5. Furthermore, the support part 12, as is evident from FIG. 17, has two wedge-shaped tips 54 and 55, provided at least at a right angle with reference to its longitudinal direction. The function of these wedge-shaped tips 54 and 55 will become evident in greater detail below.

Here, the aforementioned drive element 9 is formed by a cylindrical part from which two bearing journals 8 project transverse to the longitudinal apparatus direction, which journals are guided in a guide track 6 or 7, which is situated in the side part 2 or 3, respectively, that faces the respective bearing journal. Here, the two bearing journals 8 extend from diametrically opposite sides and are guided in guide tracks 6, 7, which run in opposite directions with reference to the longitudinal apparatus direction of the positioning apparatus 1, as is evident from FIGS. 16 and 17.

The positioning apparatus 1 furthermore comprises a catheter accommodation member 11 that is accommodated by a catheter release member 10. These two members 11 and 10 have already been discussed in detail above. Furthermore, a stabilization rib 47 that connects the side part 3 and its related pressing part 5 is evident from FIG. 17, by means of which rib the location position of pressing part 5 with reference to its side part 3 is stabilized. The stabilization rib 47 is preferably produced together with the pressing part 5 and the side part 3, in a single molding process. It should be noted here that a stabilization rib corresponding to the stabilization rib 47 is also provided on the pressing part 4 and its side part 2.

In FIG. 16, the positioning apparatus 1 is shown together with a securing part 48. This securing part 48 is releasably introduced into the interstice between the two pressing parts 4 and 5 that was mentioned above in connection with FIG. 17. The interstice in question represents an accommodation opening 50 for the securing part 48. In FIG. 17 it is shown how the securing part 48 is taken out of this accommodation opening 50. In this regard, the securing part 48 is shown in two different perspective representations. These two perspective representations are supposed to make the more detailed structure of the securing part 48 evident, for one thing, and for another, they are supposed to make it clear that the securing part 48 can be releasably introduced from both sides of the positioning apparatus, into its accommodation opening 50, in other words not only from the front side evident from FIGS. 16 and 17, with the side part 2, but also from the rear side with the side part 3.

By means of the securing part 48 releasably introduced into the accommodation opening 50 of the positioning apparatus 1, it is ensured that unintentional movement of the two pressing parts 4, 5 can be prevented by means of blocking compression. In this way, a positioning apparatus 1 that can be handled in particularly secure manner is made available. Only when the securing part 48 has been taken out of the accommodation opening 50 of the positioning apparatus 1 can its pressing parts 4, 5 be compressed and the positioning apparatus 1 be activated as a result.

With regard to the securing part 48, it should still be noted that this has a handle part 49 that projects outward from it with reference to FIGS. 16 and 17 and two insertion parts 51, 52, which are directed inward toward the accommodation opening 50 with reference to FIGS. 16 and 17, and here are configured in segment shape in cross-section. A continuous elongated cavity having contact surfaces that lie opposite one another is formed between these insertion parts 51, 52. The two segment-shaped insertion parts 51, 52 have three empty chambers that are connected with one another, in each instance. With the contact surfaces that have just been mentioned, the two insertion parts 51, 52 of the securing part 48 lie against the wedge-shaped tips 54 and 55 of the support part 12 when the securing part is introduced into the accommodation opening 50. These wedge-shaped tips 54, 55 more or less center the securing part 48 during its introduction into the accommodation opening 50 of the positioning apparatus 1.

The two insertion parts 51, 52 are furthermore provided with a clamping projection or engagement projection 53, in each instance, at diametrically opposite locations—here, in the center. With these clamping projections or engagement projections 53, it is possible to secure the securing part 48 that has been introduced into the accommodation opening 50 of the positioning apparatus 1 to prevent it from falling out of this accommodation opening 50. This is because the clamping projections or engagement projections 53 in question get into the accommodation opening 50 of the positioning apparatus 1, during introduction of the securing part 48 into the accommodation opening 50 of the positioning apparatus 1, only under pressure exertion by way of an edge region of the side parts 2, 3 that delimits the accommodation opening 50, in each instance, and must be pulled out of the accommodation opening 50 again, with the insertion parts 51, 52, overcoming a corresponding pressure, in order to pull the securing part out of the accommodation opening 50 of the positioning apparatus 1.

At this point, it should still be noted that the securing part 48 can also be implemented in a fundamentally different manner than is evident from FIGS. 16 and 17. Thus, the function of the securing part 48 described can also be implemented by means of a releasable locking device, for example, such as a part inserted through the two side parts 2 and 3 or through the two pressing parts 4 and 5.

Figure 18:
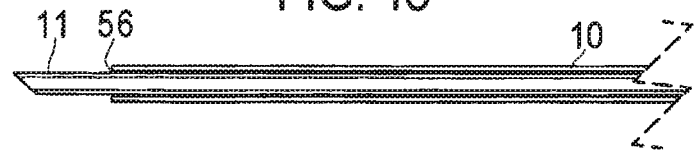
FIG. 18 shows, in a sectional view, not to scale, the region between a catheter accommodation member and a catheter release member of a positioning apparatus according to the invention.

The region between the catheter accommodation member 11 and the catheter release member 10 of a positioning apparatus 1 according to yet another practical embodiment of the invention is shown in FIG. 18, in a sectional view, not to scale.

Here, a radiation-sensitive detection layer 56 is provided between the catheter accommodation member 11 and the catheter release member 10. By irradiation of this region by means of a radiation to which the detection layer 56 responds, the distal end region of the positioning apparatus 1 according to the invention, by which the catheter to be positioned in an individual is carried, can be made visible on a monitor by means of an imaging method. Preferably, here the radiation sensitivity for X-rays is utilized. For this purpose, the radiation-sensitive detection layer in question consists of gold, platinum or of a platinum-iridium alloy, which is applied either to the outside of the catheter accommodation member 11 or to the inside of the catheter release member 10.

In conclusion, the following should still be noted. In the first and second embodiments of the invention, the catheter was released from its catheter accommodation member, in each instance, in that the related catheter release member was pushed over the catheter accommodation member. In contrast, in the third and fourth embodiments of the invention, the catheter was released from its accommodation member in that the catheter accommodation member in question was retracted into its related catheter release member. In this connection, however, it should be noted that a positioning apparatus according to the invention can also have a structure such that a hose-shaped or cylindrical catheter release member is accommodated in the catheter accommodation member, which is configured in hose shape. The movements of such a catheter accommodation member and such a catheter release member can fully correspond to the movements of the catheter accommodation members and catheter release members described above.

REFERENCE SYMBOL LIST 1 positioning apparatus
2 side part
3 side part
4 pressing part
5 pressing part
6 guide track
7 guide track
8 bearing journal
9 drive element
10 catheter release member
11 catheter accommodation member
12 support part
13 guide track depression
13' guide track depression
13" guide track depression
14 catheter
15 connection part
16 pressing part
17 pressing part
18 connection part
19 support arm
20 support arm
21 opening
22 opening
23 articulation member
24 articulation member
30 holder
31 activation member
32 bearing journal
33 guide track
34 pushing member
35 oblong hole
40 accommodation body
41 pivoting member, lever
42 pushing member
43 oblong hole
44 bearing opening
45 accommodation opening
46 bearing journal
47 stabilization rib
48 securing part
49 handle part
50 accommodation opening
51 insertion part
52 insertion part
53 clamping projection or engagement projection
54 contact tip
55 contact tip
56 detection layer

The invention claimed is:

1. A positioning apparatus for a medical catheter (14) to be positioned in a body opening or body cavity of an individual, comprising
   an elongated tubular or hose-shaped catheter accommodation member (11), by one end of which the catheter (14) to be positioned can be accommodated,
   an elongated catheter release member (10) accommodated within or outside of the catheter accommodation member (11) and displaceable in the longitudinal direction of the catheter accommodation member,
   and a movement mechanism provided between the catheter accommodation member (11) and the catheter release member (10), having a movement conversion device (2 to 9, 12) by means of which the catheter accommodation member (11), with the catheter (14) accommodated by it, and the catheter release element (10) can be displaced relative to one another in a longitudinal apparatus direction, with release of the catheter (14) from the catheter accommodation member (11), wherein the movement conversion device (2 to 9, 12) has an activation member (4, 5) by means of which a transversal movement or a pivoting movement exerted transverse to the said longitudinal apparatus direction can be converted into a longitudinal movement that runs in the said longitudinal apparatus direction, wherein the activation member (4, 5) has first and second pressing parts (4, 5) that are connected with one another by means of a connection part and can be compressed in the direction toward the connection part, wherein the connection part is firmly connected with the catheter accommodation member (11) or the catheter release member (10), and wherein the catheter release member (10) or the catheter accommodation member (11) has at least one bearing journal (8) that projects away from the catheter release member or catheter accommodation member and is accommodated in a first guide track (6, 7) of the activation member (4, 5), the first guide track (6, 7) being configured such that the catheter release member (10) and the catheter accommodation member (11) are displaceable relative to one another in the longitudinal apparatus direction in response to compression of the first and second pressing parts (4, 5).

2. The positioning apparatus according to claim 1,
wherein the activation member further comprises a second guide track,
wherein the first pressing part has a first side part and the second pressing part has a second side part, wherein the first and second side parts (2, 3) project away from the first and second pressing parts at an angle,
wherein the first guide track is accommodated in the first side part and the second guide track is accommodated in the second side part, and
wherein the first and second guide tracks (6, 7) run in opposite directions to each other with reference to the longitudinal apparatus direction.

3. The positioning apparatus according to claim 1,
wherein the first and second pressing parts (4, 5) can be protected by means of a securing part (47) that blocks their unintentional movement.

4. The positioning apparatus according to claim 3,
wherein the securing part (47) forms an insertion part that can be releasably accommodated by an opening (50) formed between the first and second pressing parts (4, 5).

5. The positioning apparatus according to claim 1,
wherein a radiation-sensitive detection layer is provided between the catheter accommodation member (11) and the catheter release member (10).

* * * * *